(12) United States Patent
Livchak et al.

(10) Patent No.: US 9,393,338 B2
(45) Date of Patent: Jul. 19, 2016

(54) AIR PURIFICATION DEVICES METHODS AND SYSTEMS

(75) Inventors: Andrey V. Livchak, Bowling Green, KY (US); Rick A. Bagwell, Scottsville, KY (US)

(73) Assignee: OY HALTON GROUP LTD., Helsinki (FI)

( * ) Notice: Subject to any disclaimer, the term of this patent is extended or adjusted under 35 U.S.C. 154(b) by 537 days.

(21) Appl. No.: 13/988,033

(22) PCT Filed: Nov. 18, 2011

(86) PCT No.: PCT/US2011/061559
§ 371 (c)(1),
(2), (4) Date: Jun. 17, 2013

(87) PCT Pub. No.: WO2012/068569
PCT Pub. Date: May 24, 2012

(65) Prior Publication Data
US 2013/0291735 A1    Nov. 7, 2013

Related U.S. Application Data

(60) Provisional application No. 61/414,935, filed on Nov. 18, 2010.

(51) Int. Cl.
*A61L 2/00* (2006.01)
*A61L 9/20* (2006.01)
(Continued)

(52) U.S. Cl.
CPC ... *A61L 9/20* (2013.01); *F24F 1/01* (2013.01); *F24F 3/16* (2013.01); *F24F 13/00* (2013.01); *F24F 13/28* (2013.01); *A61L 2209/111* (2013.01); *A61L 2209/16* (2013.01);
(Continued)

(58) Field of Classification Search
USPC ............................................. 165/48.1; 96/224
See application file for complete search history.

(56) References Cited

U.S. PATENT DOCUMENTS

| | | | |
|---|---|---|---|
| 6,692,350 B1 | 2/2004 | Moy | |
| 2002/0031460 A1* | 3/2002 | Kulp | F24F 3/16 422/292 |

(Continued)

FOREIGN PATENT DOCUMENTS

| | | |
|---|---|---|
| EP | 1688151 A1 | 8/2006 |
| EP | 2640428 A4 | 4/2014 |

(Continued)

OTHER PUBLICATIONS

Office Action issued Sep. 29, 2014, in Chinese Patent Application 201180064999.0.

(Continued)

*Primary Examiner* — Duane Smith
*Assistant Examiner* — Adam W Bergfelder
(74) *Attorney, Agent, or Firm* — Potomac Law Group PLLC

(57) ABSTRACT

A device and method for air purification used in cooling, heating and air ventilation systems. The device has at least one UV light source positioned on an inside portion of a movable access panel so that it moves with the access panel from a first position where the UV source directs UV light towards the inside of the system to purify the air stream inside and to remove contaminants from the surfaces inside the system, to a second position where the UV source directs UV light towards the space surrounding the system so that it purifies the air in the room where the system is mounted.

6 Claims, 12 Drawing Sheets

(51) Int. Cl.
*F24F 1/01* (2011.01)
*F24F 3/16* (2006.01)
*F24F 13/28* (2006.01)
*F24F 13/00* (2006.01)
F24F 13/06 (2006.01)
F24F 1/00 (2011.01)

(52) U.S. Cl.
CPC . *F24F2001/0037* (2013.01); *F24F 2003/1667* (2013.01); *F24F 2013/0616* (2013.01); *F24F 2221/14* (2013.01)

(56) References Cited

U.S. PATENT DOCUMENTS

| 2004/0055620 | A1 | 3/2004 | Fencl et al. |
| 2006/0177356 | A1 | 8/2006 | Miller |
| 2008/0232116 | A1 | 9/2008 | Kim |
| 2008/0265179 | A1* | 10/2008 | Havens ............... A61L 2/10 250/492.1 |
| 2009/0101930 | A1* | 4/2009 | Li ................... F21K 9/135 257/98 |
| 2009/0129974 | A1 | 5/2009 | McEllen |
| 2010/0032589 | A1 | 2/2010 | Leben |
| 2013/0291735 | A1 | 11/2013 | Livchak et al. |

FOREIGN PATENT DOCUMENTS

| WO | WO 2004101101 A2 | 11/2004 |
| WO | WO 2012/068569 A1 | 5/2012 |

OTHER PUBLICATIONS

International Search Report and Written Opinion for International Application No. PCT/US2011/061559.
Office Action issued May 5, 2015, in Chinese Patent Application 2011800649990.
Examination Search Report issued Mar. 26, 2015, in Canadian Patent Application No. 2,818,444.
Extended European Search Report for International Application No. PCT/US2011/061559 dated Mar. 5, 2014.

\* cited by examiner

151

152

AIR PURIFICATION DEVICES METHODS AND SYSTEMS

REFERENCE TO RELATED APPLICATIONS

This application claims the benefit of U.S. Provisional Application No. 61/414,935, entitled "Chilled Beam with Air Purification," filed on Nov. 18, 2010, the entirety of which is hereby incorporated by reference herein.

FIELD OF THE INVENTION

This invention relates to air purification and ventilation systems in general and in particular to terminal units employing ultraviolet (UV) radiation to filter or decontaminate occupied spaces.

DISCLOSURE

Chilled beams are components of air treatment systems used for cooling and air ventilation processes. They are suited for large and small occupied spaces in all types of buildings where comfort and ventilation are required. Chilled beams have various known advantages. For example, the cooling capacity can be partly satisfied by a cold water piped to the chilled beam rather than requiring all of the cooling load to be satisfied by air handlers sized to carry sufficient volumes of cooled air. As such, only the ventilation load need be handled by the air handling system. Also, chilled beams are suitable for mounting in ceilings or mounted flush with a suspended ceiling, but since they are standalone components, they can be mounted in many different ways. Latent load must be handled by distributed air, which is fresh, because chilled beams cannot satisfy the latent load the terminal units themselves because they are not adapted for handling condensate.

Chilled beams can be passive or active. Passive chilled beams depend on natural convection and usually consist of a coil (air treatment device) in a plenum box that is recessed or hung from a ceiling. In an air cooling mode, chilled water flows through the coil and the warm air rising toward the coil is cooled causing it to fall into the room in which the beam is installed. Depending on whether the air needs to be cooled, heated or just ventilated, the coil treats the air accordingly. Active chilled beams also contain a coil in the plenum box hung or suspended from a ceiling but they use ventilation air introduced into the beam plenum through small air jets to magnify the natural induction of air.

An example of a chilled beam 100 is illustrated in FIGS. 1A and 1B. Chilled beam type terminal unit 100 is shown from below in FIG. 1A and in section in FIG. 1B. The ceiling-mounted (ceiling indicated at 130) terminal unit 100 contains a plenum box 104 with a primary ventilation air connection collar 106 connectable to a flexible air duct (not shown) or an adjacent beam module to distribute fan-pressurized air into the system and specifically into a primary air plenum 108. Primary ventilation air is pushed through primary air nozzles 114 which generates jets 130. The jets 130 induce a flow of air 124 in a flow passage 116. The plenum box 104 is attached to the ceiling 132 by a suitable mount 134. Flanges 26 define the flow passage 116. The induced portion of the flow is drawn from warm room air 110 which passes through a cooling coil 118 and joins the primary air jets 130 as indicated at 128. The combination of primary and induced air makes up the flow 124 which exits as indicated at 112. The flow 112 preferably has appreciable velocity to allow it to cool the occupied space conditioned by the chilled beam 100. Thus a cool flow of locally-chilled recirculated air and a primary stream are combined in the flow 112 to cool the occupied space.

As shown in FIGS. 2A and 2B, chilled beams 151 and 152 can take a variety of shapes. They come in passive and active configurations. In passive types, the energy for moving the air through the system comes from natural convection. In active systems, induction is created by pressurized jets of air. The embodiment 151 is symmetrical and generates jets of air bilaterally to both sides of the beam. The embodiment 152 is asymmetric and generates a jet or jets to one side so that it can be located close to a wall without blowing air at the wall.

According to embodiments, the disclosed subject matter includes a combined cooling, heating and air supply treatment system for a suspended ceiling installation, comprising: a housing including an air treatment device and a movable access member which is configured to form an enclosure with the housing when in a first position and to allow access to the air treatment device when in a second position; wherein the access member includes a plurality of openings configured to permit passage of ambient air from a space outside of the enclosure into the enclosure, and passage of air treated by the air treatment device from the enclosure to the space outside of it.

The access member may be movable from the first position to the second position by pivotal movement. At least one UV light source may be attached to an inside portion of the access member, such that the UV light source moves with the access member. The first position the at least one UV light source may be configured to direct light towards an inside of the enclosure and in the second position the at least one UV light source is configured to direct light towards the space outside of the enclosure. At least a portion of the plurality of openings may include elongated channels to direct ambient air towards the air treatment device and to block direct UV light from escaping the enclosure. A motion sensor may be configured to shut-off the at least one UV light source responsively to a detection of motion in the space outside of the enclosure. A remote controlled device may be configured to turn the at least one UV light source on and off remotely. The access member may include a first layer with a plurality of first openings and a separate second layer with a plurality of second openings, wherein the layers are positioned such that the plurality of first openings are shifted relative to the plurality of second openings so that ambient air can flow through the first and then the second layer unobstructed and such that direct UV light does not pass between the first and second openings.

According to embodiments, the disclosed subject matter includes an air treatment system comprising: a housing including an air treatment device and a movable access member which is configured to form an enclosure with the housing when in a first position and to allow access to the air treatment device when in a second position; wherein the access member includes a plurality of openings that permit passage of ambient air from a space outside of the enclosure into the enclosure, and wherein the access member includes at least one UV light source attached to an inside portion of it, such that the UV light source moves with the access member. In the first position the at least one UV light source may be configured to direct light towards an inside of the enclosure and in the second position the at least one UV light source is configured to direct light towards the space outside of the enclosure. A motion sensor may be configured to shut-off the at least one UV light source responsively to a detection of motion in the space outside of the enclosure. A remote controlled device may be configured to turn the at least one UV light source on and off remotely. The at least one UV light source may be a solid state UV light source attached to the inside portion of the access member so that it does not block the passage of ambient air into the enclosure. A UV light reflective baffle may surround the at least one UV light source to reflect UV light towards an inside of the housing and to block UV light from escaping the enclosure through the plurality of openings. At least a portion of the plurality of openings may include elongated channels to direct ambient air towards the air treatment device, and to block direct UV light from escaping the enclosure. At least a portion of said elongated channels may be coated with UV light reflecting coating to block UV light from escaping the enclosure. An exterior surface of the air treatment device and an interior surface of the housing may include a UV light absorbing coating. The access member may move from the first position to the second position by pivotal movement. The access member may include a first layer with a plurality of first openings and a separate second layer with a plurality of second openings, wherein the layers are positioned such that the plurality of first openings are shifted relative to the plurality of second openings so that ambient air can flow through the first and then the second layer unobstructed and such that direct UV light does not pass between the first and second openings.

According to embodiments, the disclosed subject matter includes an air treatment device comprising: an enclosure with at least one UV light source positioned inside the enclosure, the enclosure configured to change from a first configuration where the at least one UV light source directs light into the enclosure and a second configuration where the at least one UV light source directs light towards a space outside of the enclosure. A device as claimed in claim 20, further comprising a motion sensor configured to shut-off the at least one UV light source responsively to a detection of motion in the space outside of the enclosure. A remote controlled device may be configured to turn the at least one UV light source on and off remotely.

According to embodiments, the disclosed subject matter includes an air-treatment method comprising: moving an enclosure between a first configuration where at least one UV light source attached to an inside of the enclosure directs light into the enclosure, and a second configuration where the at least one UV light source directs light towards a space outside of the enclosure.

According to embodiments, the disclosed subject matter includes an air disinfection method comprising: directing light from at least one UV light source attached to an inside portion of an access member towards a space in an enclosure formed by the access member and a housing containing an air treatment device; and directing light from the at least one UV light source towards a space outside of the enclosure by moving the access member.

According to embodiments, the disclosed subject matter includes a method of disinfecting air in a ceiling suspended air treatment system and a space outside of the system, comprising: directing UV light towards ambient air in the system with at least one UV light source attached to an access member forming an enclosure with the system; and directing UV light towards ambient air in a space outside of the system by moving the access member so that the at least one UV light source faces the space outside of the system.

The UV lamp of any of the embodiments may be arranged to illuminate an elongate flow path and is mechanically isolated from a return air path by a transparent window with the UV lamp and elongate flow path lying on opposite sides of the window.

A secondary terminal unit may supply the primary air to the air treatment devices of any of the embodiments where the primary air including fresh air and return air. The secondary terminal unit may have UV lamps therein. The in-room air treatment devices may alternatively not have UV lamps and the UV may thus be applied to the primary air supplied to the air treatment devices by the lamps in the secondary terminal unit.

A flow straightener positioned in any of the embodiments to reduce the amount of UV light escaping the air treatment devices.

According to embodiments, the disclosed subject matter includes a chilled beam-type terminal unit, comprising: a housing with a heat exchanger configured for receiving chilled water; a flow space with UV lamps, the housing having flow directing elements arranged to direct return and supply air through the heat exchanger and out of the housing while causing light from the UV lamps to shine on the air flowing therethrough; the heat exchanger being arranged to serve as at least a portion of a light blocking mechanism and positioned between an inlet or an outlet of the housing. The heat exchanger may be of a fin-tube type. The UV clamps may be positioned to illuminate the heat transfer surfaces of the heat exchanger. A flow straighter may be positioned to block light emerging from either or both of the inlet and outlet of the housing. A window may be positioned between an air flow path and the UV lamps. A window may face an exterior of the housing and have a frequency downconverting property to convert excess UV light from the lamps escaping therethrough into visible light.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION OF FURTHER FIGURES

Figure 1A:
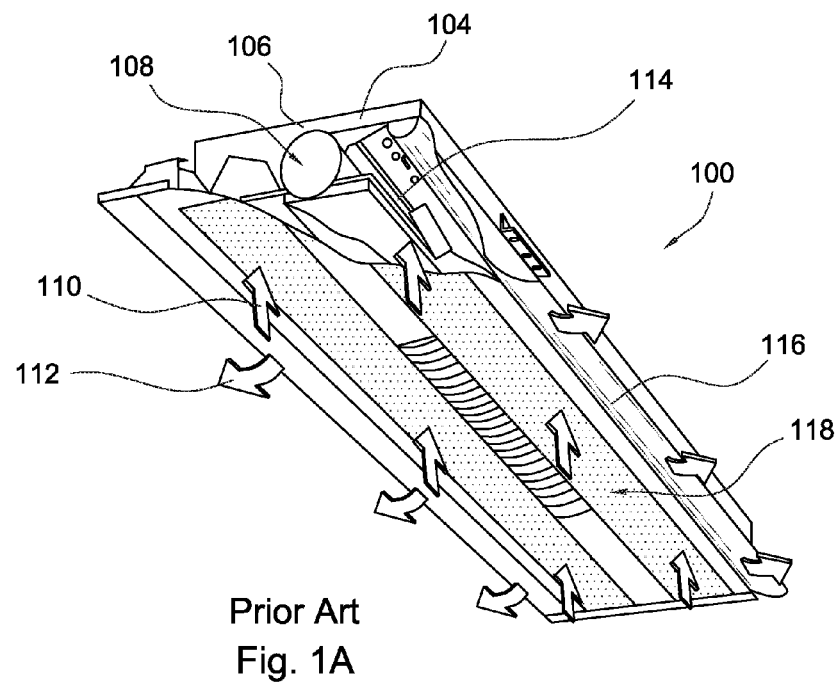
FIG. 1A is a perspective view of a conventional chilled beam.
Figure 1B:
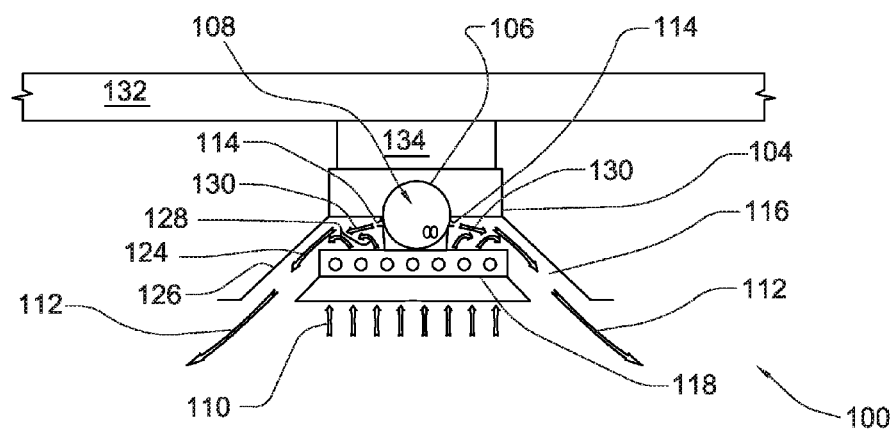
FIG. 1B shows a conventional chilled beam in cross section.
Figure 2A:
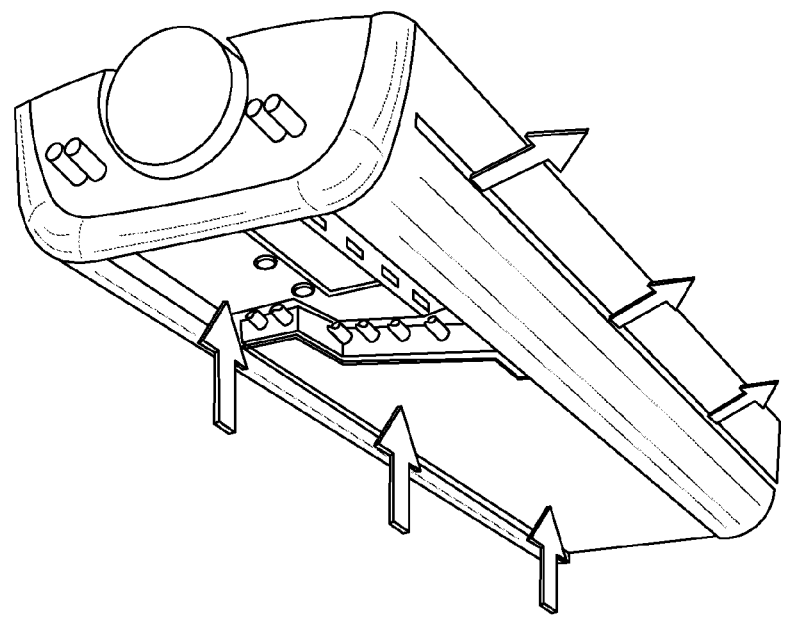
FIG. 2A is a perspective view of a symmetric chilled beam that produces bilateral jets.
Figure 2B:
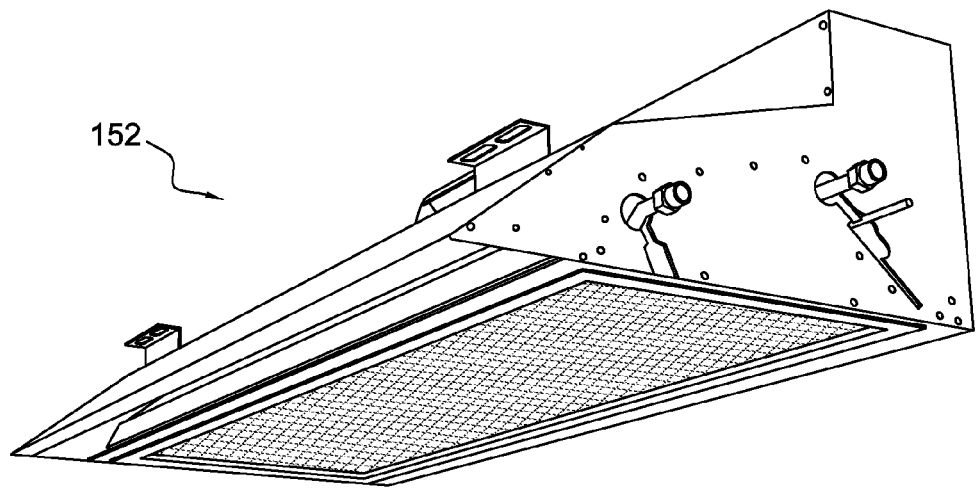
FIG. 2B is a perspective view of an asymmetric chilled beam that produces a lateral jet.
Figure 3:
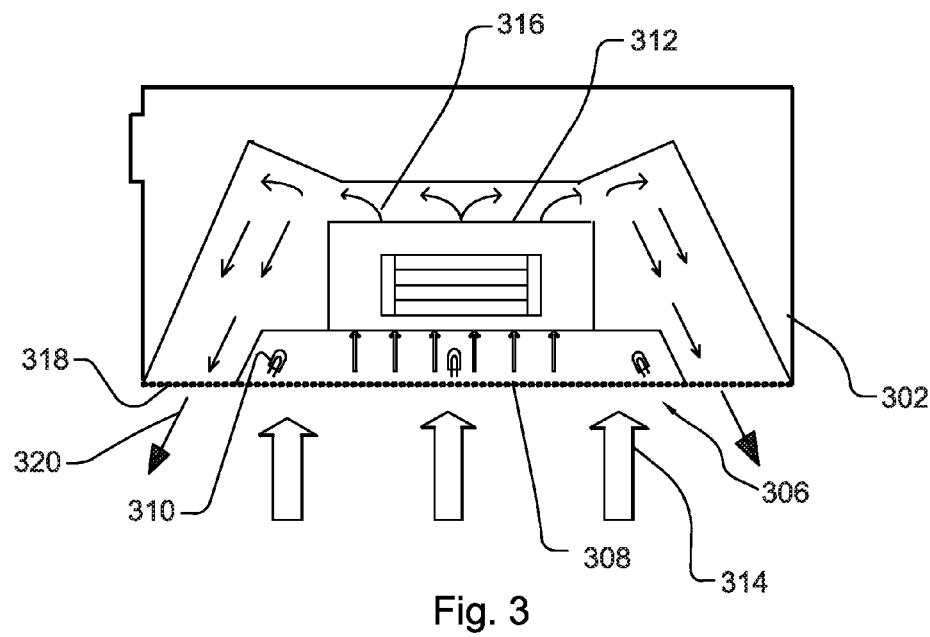
FIG. 3 is a section view of a chilled beam with an ultraviolet light source.

Referring to FIG. 3, a chilled beam unit 302 has an ultraviolet (UV) light source 306, in this embodiment a panel 308 with UV lamps mounted thereon. The UV source may be replaced by any type of UV source, such as light emitting diodes, gas-discharge tube lamps, corona discharge sources, fluorescent lamps, etc. Preferably, the panel has openings that permit the flow of air through the panel 308 to pass through a heat exchanger with a primary air induction flow unit 312 which is configured to form induction jets from primary air emitted from a pressurized duct and induce the room air 314 through the heat exchanger. The heat exchanger and primary air duct are not shown separately but a person of ordinary skill may configure them in a variety of ways to create a flow 316 of cooled room air and primary air flowing at a sufficient velocity that it is discharged from a discharge vent 318 to form a mixing jet 320 that cools the air in the room in the fashion known as mixing ventilation.

Figures 4A, 4B:
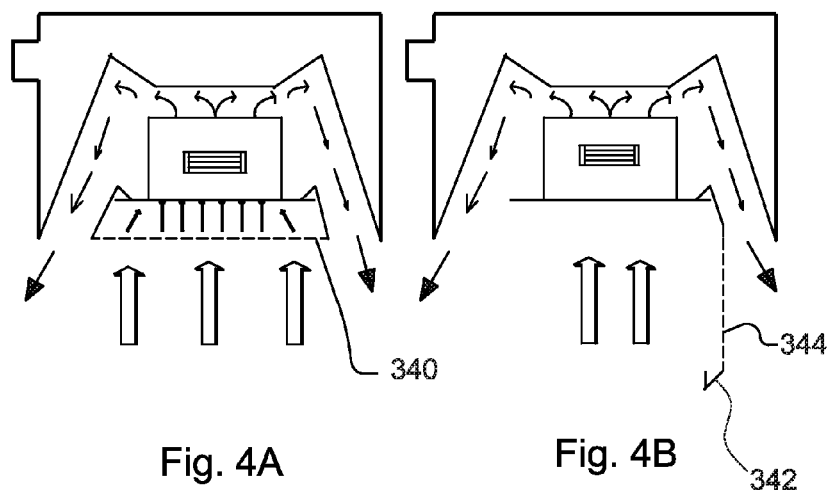
FIGS. 4A and 4B shows sections of the unit of FIG. 3 with a movable air inlet grill or panel that can support UV light sources.

FIGS. 4A and 4B shows the embodiment of FIG. 3 with a movable panel 340. The panel is shown in a closed position at 340 and in an open position at 342. The open position lowers the UV light source 308 attached to the panel 340 into an accessible position for cleaning. Openings 344 in the panel 340 admit air and are preferably shaped to block light from the UV light source (not shown in FIGS. 4A and 4B) from directly passing through the panel 340 and striking surfaces or occupants of the room.

Figure 5A:
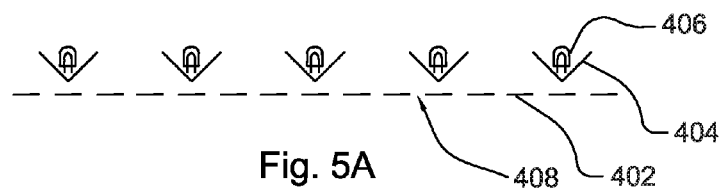
FIGS. 5A through 5C show various embodiments in section of movable inlet grilles of the unit of FIG. 4B.
Figure 5B:
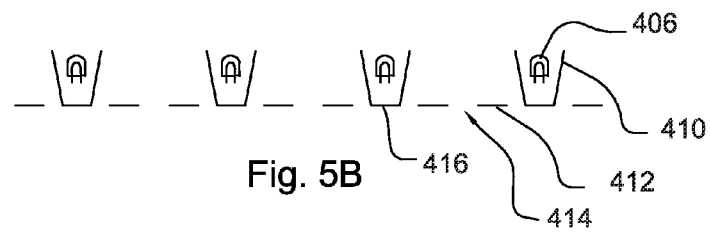
Figure 5C:
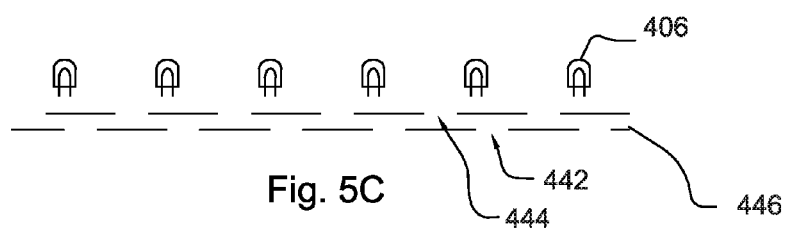

FIGS. 5A through 5C show different examples of configurations for admitting warm air through the grilles 340 or 344 of FIGS. 3 and 4A and 4B, which correspond to grilles 402, 412, 446 (the latter with layers 442/and 444) of FIGS. 4A through 4C. Lamps 406, which may be any kind of UV light source, are provided with a cup or trough 404, depending on whether the lamp is elongate such as the shape of a long gas discharge tube (going into the page of the drawing) or low aspect ratio such as an LED or round bulb. The cup or trough 404 or 410 may be provided to block light escaping through the air inlet openings 408 or 414 of the panel 402 or 412. In embodiment of panel 446, two panels are arranged to allow air to pass through respective openings in each panel while the overlapping helps to block light escaping.

Figure 6A:
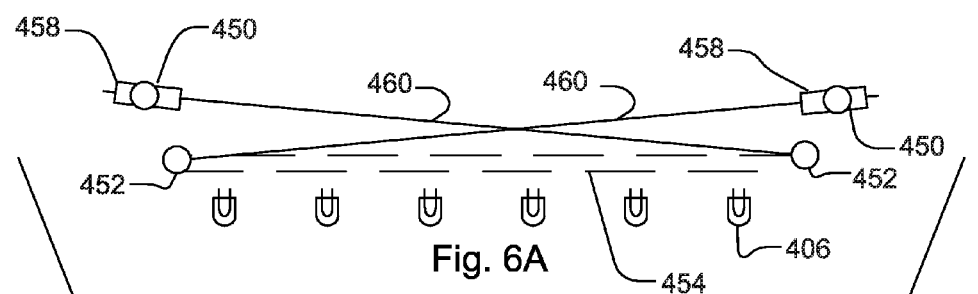
FIGS. 6A and 6B show an inlet grill panel carrying UV sources that can be flipped to face a room in which the chilled beam is installed.
Figure 6B:
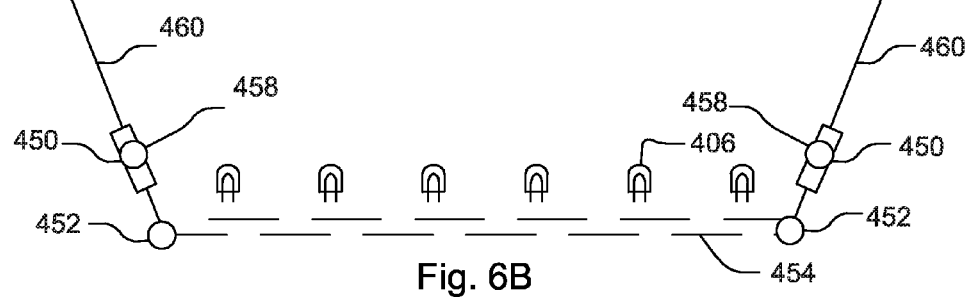

FIGS. 6A and 6B shows a grill 454 with lamps thereon that may be moved down for cleaning and, optionally, also permit the grill 454 to flipped 180 degrees to permit the UV lights 406 thereon to illuminate surfaces in a room (for example to sterilize surfaces of an unoccupied room). In a method, a hospital room is sterilized in this manner between patients. A proximity sensor, video camera with occupancy recognition computer, or other device is provided to control power to the UV lamps to ensure that occupants are not irradiated by the lamps. In the embodiment of FIGS. 6A and 6B, rods 460 are attached by at pivots 452 to panel 454. The rods 460 each pass through a tightly fitted (for example by means of a plastic sleeve linear bearing) opening of a slider 458 mounted to a pivot 450 attached to the chilled beam housing. This arrangement allows the panel 454 to be drawn down for cleaning or also rotated to the position of FIG. 6A for irradiating a space. In normal operation the panel 454 is rotated to the position shown in FIG. 5C.

Figure 7A:
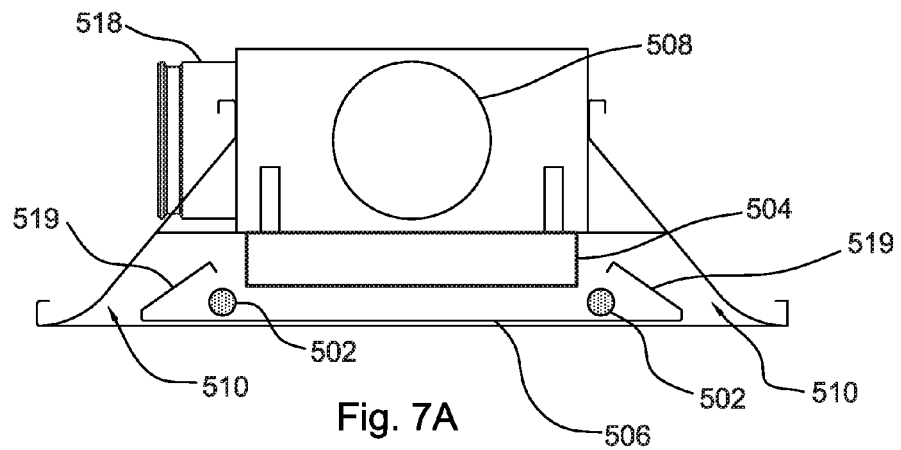
FIGS. 7A and 7B show a chilled beam with a UV source mounted on a panel that can be tilted to permit cleaning or to expose an interior of a room to UV illumination for decontamination.
Figure 7B:
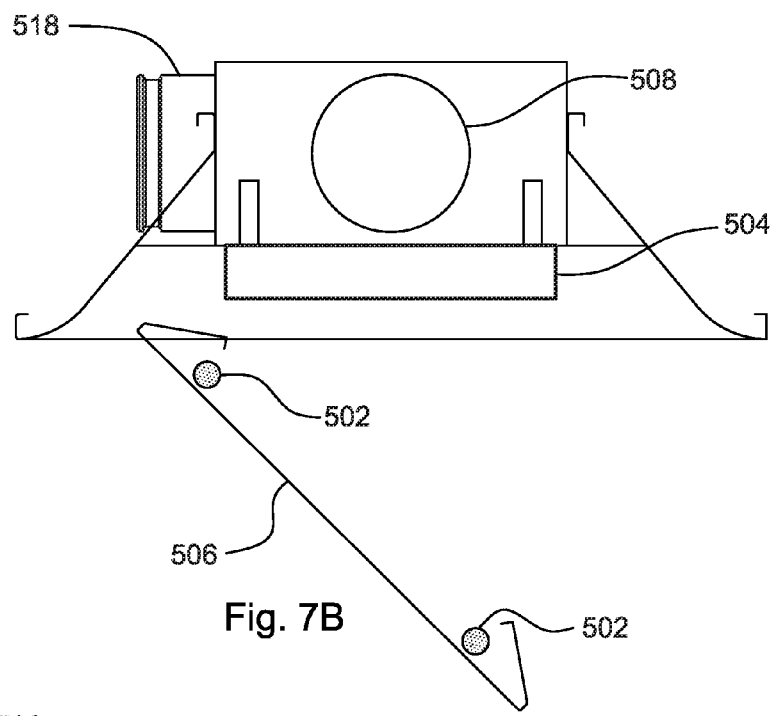
Figure 7C:
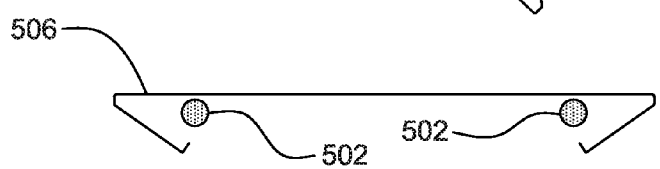
FIG. 7C shows a variation of the embodiment of FIGS. 7A and 7B in which a panel can be rotated 180 degrees to illuminate room surfaces with UV.

FIGS. 7A and 7B show another chilled beam embodiment. A fresh air inlet collar 518 attaches to a duct system that supplies ventilation air to a channel 508 from which jets are emitted inducing flow out of outlet channels 510. Recirculated room air is drawn through an inlet panel 506 and through a heat exchanger 504 by the suction caused by the jets. The inlet panel, which may have openings provided toward a center thereof to allow air therethrough supports UV light sources 502. A portion 519 of the panel 506 acts as a shade to prevent direct light escaping the chilled beam. The panel 506 can be pivotally mounted to permit access to the UV light sources for cleaning and can be flipped over as shown in FIG. 7C for irradiating surfaces of a conditioned space below.

Figure 8A:
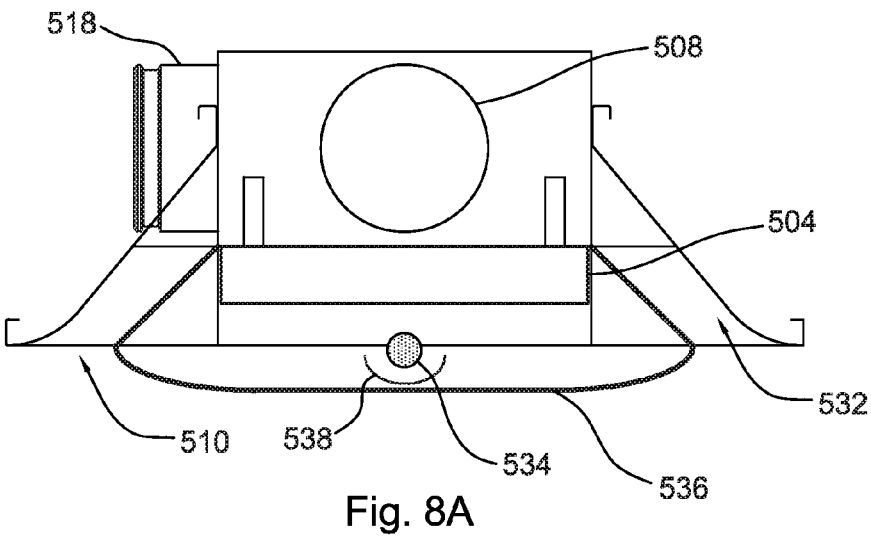
FIGS. 8A and 8B show another chilled beam with a UV source mounted on a panel that can be tilted to permit cleaning or to expose an interior of a room to UV illumination for decontamination.
Figure 8B:
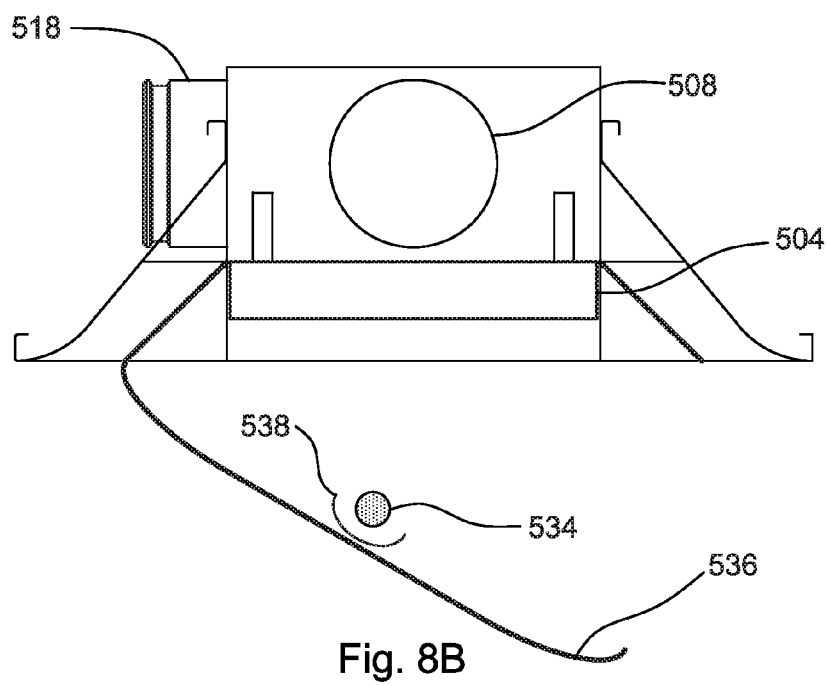
Figure 8C:
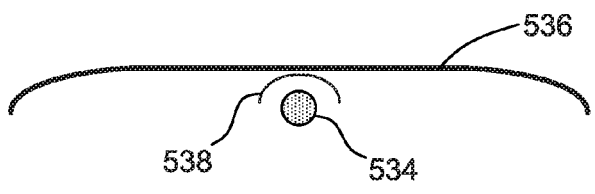
FIG. 8C shows another variation of the embodiment of FIGS. 8A and 8B in which a panel can be rotated 180 degrees to illuminate room surfaces with UV.

FIGS. 8A and 8B show another chilled beam embodiment. A fresh air inlet collar 518 attaches to a duct system that supplies ventilation air to a channel 508 from which jets are emitted inducing flow out of outlet channels 532. Recirculated room air is drawn through an inlet panel 536 and through a heat exchanger 504 by the suction caused by the jets. The inlet panel 536, which may have openings provided toward a center thereof to allow air therethrough supports UV light source 534. A portion 538 of the panel 536 acts as a shade to prevent direct light escaping the chilled beam. The panel 536 can be pivotally mounted to permit access to the UV light sources for cleaning and can be flipped over as shown in FIG. 8C for irradiating surfaces of a conditioned space below.

Preferably the embodiments disclosed may employ UV radiation in the 240-280 nm range. This may have germicidal applications to kill bacteria, mold, yeast, viruses, and any other type of microbial contaminants. Germicidal UV lamps may experience constant airflow which removes heat which may cause the mercury inside certain types of lamps to condense and the emission of germicidal wavelength to decrease. The lowering of internal temperature may cause the lamp components to degrade quicker. UV lamps in air conditioning systems may be positioned in such a way as to be shield them from airflow and to direct UV light towards the static elements inside the system, but not such as to cool the light sources themselves.

Embodiments of the disclosed subject matter include a chilled beam to improve air quality and occupant health in an environment where air treatment systems are utilized, by effectively and efficiently eliminating mold, bacteria and other contaminants that deposit on the inside surfaces of the air treatment system. Embodiments of the disclosed subject matter also include a chilled beam to effectively and efficiently eliminate air contaminants from the airstream inside the air treatment system as well as to eliminate air contaminants in the ambient air in the environment surrounding the system. Embodiments of the disclosed subject matter further include a chilled beam that uses germicidal UV lights to effectively and efficiently destroy bacteria, mold, and any other contaminants that deposit on surfaces, and to position the UV lights inside the air treatment system in such a way as to destroy the contaminants inside the system as well as the air contaminants in the environment outside the system.

Embodiments of the disclosed subject matter include a method of utilizing UV light sources positioned in a particular manner relative to the air treatment system such that the coil and other inside components and surfaces are irradiated with UV light to effectively destroy and remove contaminants deposited thereon. Additionally, UV light sources are preferably positioned relative to the system in such a way as to irradiate the airstream inside the system before it reaches the air treatment device. Moreover, the present invention utilizes UV light sources preferably positioned relative to the system in such a way as to irradiate the space outside the system to remove contaminants from the air before the air enters the system.

Embodiments of the disclosed subject matter include an air treatment system has a housing including an air treatment device and a movable access member which is configured to form an enclosure with the housing when in a first position and to allow access to the air treatment device when in a second position, wherein the access member includes a plurality of openings configured to permit passage of ambient air from the space outside of the enclosure into the enclosure, and wherein the access member includes at least one UV light source attached to an inside portion of it, such that the UV light source moves with the access member.

An air treatment system that performs combined cooling, heating and air supply for a suspended ceiling installation, where the movable access member permits passage of ambient air from the space outside of the enclosure into the enclosure as well as passage of air treated by the air treatment device from the enclosure to the space outside of the enclosure. In another embodiment, the access member moves from the first position to the second position by a pivotal movement and in the first position the UV light source is configured to direct light towards the inside of the enclosure and in the second position the UV light source is configured to direct light towards the space outside of the enclosure. In another embodiment, the plurality of openings in the access member may include elongated channels so that the ambient air is directed (channeled) towards the coil (air treatment device) and the direct UV light from the sources are blocked from escaping the enclosure. The channels may be coated with a UV reflecting coating to block UV light from escaping the enclosure. In another embodiment, the system may comprise a motion or occupancy sensor to sense the presence of body in the room where the system is used, and in case presence is detected to automatically shut-off the UV light sources. In one embodiment the shutting off of the light sources may be done using a remote switch that is either wired or wireless.

The access member may include two layers, each with its own plurality of openings, the layers positioned in such a way as to have the plurality of openings shifted (offset) relative to each other, so that ambient air can flow through the layers and such that the direct UV light does not pass through the layers and does not escape the enclosure. Reflective baffles may surround the UV light sources to reflect UV light towards the inside of the housing and to block UV light from escaping the enclosure through the plurality of openings in the access member. The exterior surface of the coil (air treatment device) and the interior surface of the housing may include a UV light absorbing coating. The UV light sources may be solid state UV light sources, positioned on the inside portion of the movable access member so that they don't block the airflow inside the system.

An air treatment system has: an enclosure with at least one UV light source positioned inside the enclosure. The enclosure is configured to change from a first configuration where the UV light source directs light into the enclosure and a second configuration where the UV light source directs light towards a space outside of the enclosure by selectively rearranging the enclosure. Preferably, the system also has a motion sensor that is configured to shut-off the UV light source in response to a detection of motion in the space outside of the enclosure. Additionally, the system may include a remote controlled device to turn the UV light sources on and off using a switch that may be wired or wireless. The system may also include baffles surrounding the UV light to reflect the UV light towards the inside of the enclosure and to block UV light from escaping the enclosure. Preferably, the enclosure has a plurality of elongated channels to direct ambient air towards the air treatment device and to block direct UV light from escaping the enclosure through the channels.

An air treatment method may implement any of the above systems. An air disinfection method may implement any of the above disclosed systems.

The foregoing chilled beam embodiments may form a combined cooling, heating, and supply air treatment system (chilled beam) attachable to a ceiling of a room using movable brackets or any other suitable mounting elements. The systems may include a plenum box with a primary air connection collars and a duct system interconnecting a source of ventilation air (which may be fresh or filtered and reconditioned recirculation air or a mixture thereof) other multiple modules in the system. Together one or more modules may distribute the primary ventilation air to a conditioned space and provide sensible cooling in the space. The overall system may include many occupied spaces. The air handling system may employ a fan that blows the primary ventilation air into the system.

The pressurized air from the plenum 11 is pushed towards the induced air channels through the primary air nozzles which may take any suitable for including simple openings to venturi nozzles or directable grilles. The pressurized jets of air discharging from the induced air channels through discharge nozzles causes a negative pressure around the space surrounding the nozzles which then creates an induction in the ambient secondary air that naturally rises from the room towards the chilled beam forcing the rising air through a heat exchanger. UV light sources generate ozone and radiation that cleans the air and irradiates the heat exchanger surfaces. In embodiments, the UV sources are positioned to irradiate heat exchanger surfaces completely.

Secondary air may be contaminated with air pollutants and microorganisms that are present in the environment where the chilled beam is used. This contaminated air enters through the perforations panels of the embodiments. The air flows through the heat exchangers of the embodiments. The heat exchangers can be a combination of heating and/or cooling coils of different lengths depending on the application, and the coils may contain a plurality of thin fins. One or a plurality of UV light sources are positioned on the inside of the access panels using any suitable means such as support clips. The UV light sources are configured to illuminate the airflow before it hits the heat exchanger as well as the heat exchanger.

Over time, the coil fins collect dust particles, bacteria, and microorganisms, which deposit and stick to the surface of the coil. Removing the contaminants from the air before it hits the coil helps eliminate additional deposits. The germicidal light from the UV sources directly irradiate the air treatment devices, thereby destroying the contaminants, such as mold, bacteria, microorganism, etc., that deposited on its surface. The surface of the coil and the inside surface of the chamber may also be coated with a UV absorbing material layer, such as, titanium dioxide or any other suitable material, to absorb UV rays more efficiently and to eliminate stray UV light from reflecting back towards the access panel 1 and accidentally escape the chamber.

The heat exchanger heats or cools the induced air and once air leaves the heat exchanger, it forms a treated air jet by incorporating momentum from the primary air jets. The treated air enters the induced air channels and forms an induced flow of primary ventilation air and treated (chilled or heated) air jet. The chilled (heated/ventilated) air jets is pushed through the discharge channels towards the space surrounding the chilled beam.

The UV light sources may be positioned in such a way as to illuminate the return chilled air in the discharge channels before the chilled air jet leaves the system and before it is distributed into the surrounding environment. UV can be provided downstream of the heat exchanger in addition or as an alternative.

The access panel may be made of durable metal sheet and may contain a plurality of perforations. The access panels may be a perforated metal grill. The perforations may have different sizes and shapes, depending on the environment in which the system is used. The access panel 1 may include inlet vanes oriented to direct the airflow towards the heat exchanger and block the UV light from the UV light sources from escaping the mixing chamber through openings. For example, the openings may form conical shapes formed by punching that define small channels and help block light escaping.

As described, the access panels may be pivotally mounted to the beam plenum so that it can be opened, closed, turned and removed without using special tools. In this first exemplary embodiment, the access door is flush with a hung false ceiling panel, so that the discharge nozzles are part of the access panel and the pressurized air jets and the treated air jet leave the system through side end portions of the access panel perforations.

The access panel can be moved from a first position where it forms a closed enclosure with the mixing chamber, to a second position where the access panel is opened and allows easy access to the heat exchanger as well as the inside of the mixing chamber. The plurality of UV light sources are attached to an inside portion of the access panel using, for example, separate support clips 16 to hold each source by its socket, so that each light source can be removed individually and easily, but can still move together with the access panel.

The UV sources may be positioned so as to face the interior of the mixing chamber. When the UV sources are turned on, the UV light is directed towards the interior of the enclosure and irradiates the coils, the induced secondary airflow, as well as the turning vanes of air that are created around the UV sources. Any number and type of UV sources may be used to accomplish the desired result. Conventional mercury UV lamps, UV LEDs or any other solid state UV light sources may be used.

Exposure to germicidal UV light is harmful to people, so before the room is exposed to the UV light, a motion or occupancy sensor (not shown) installed in the system, signals whether there is anybody in the room. A wired or wireless switch (not shown) will automatically turn off the lights if access panel is accidentally opened when someone is in the room and could be exposed to harmful radiation.

Figure 9A:
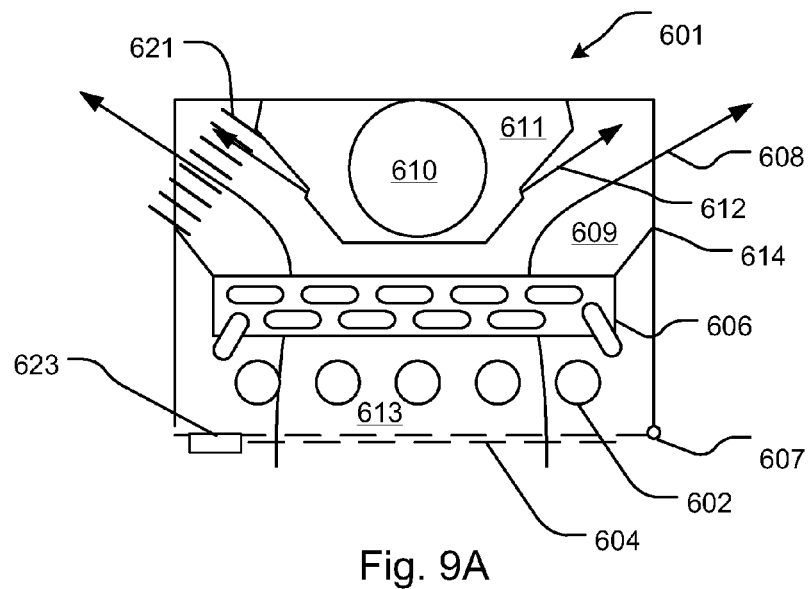
FIGS. 9A and 9B show chilled beams with UV according to further embodiments of the disclosed subject matter.

Referring now to FIG. 9A, an inlet or connection collar 610 supplies primary air to a plenum 611 that runs along the length of a chilled beam terminal unit 601. A heat exchanger 614 (fin tube type for example) cools air rising into intake grill 604 which has offset light-blocking elements, figuratively indicated at 604, but conforming to any of the embodiments described elsewhere in the present disclosure. Lamps 602 generate UV light, for example, UVC or germicidal wavelengths of UV. Light impinges the surfaces of the heat exchanger 606 reducing the risk of the formation of pathogenic cultures on these surfaces. The intake grill forms a hatch that pivots on a hinge 607 to permit access to the lamps 602. Although not shown explicitly, the lamps can be supported by any suitable mechanism to position them such that they cause UV light to impinge the heat exchange surfaces of heat exchanger 606. Air flows through the grill 604, past the lamps and through the heat exchanger 606 into the space 609 in which the jet 612 is generated from primary air in the plenum 611. The jet induces a flow in the space 609 causing a negative pressure in the space 609 that draws air through the grill 602, lamps, 602, and heat exchanger 606. A flow that includes primary and secondary (entrained) flow 608 is forced upwardly and outwardly as indicated at 608. The lamps also provide germicidal effect on the interior surfaces defining the flow passages 609, 613 of the chilled beam 601.

The fins of a fin tube heat exchanger 606 design may provide a light blocking effect by ensuring that only light directed parallel to the planes of the fins can enter the space 690 and then only in the direction of the surfaces of the fins. In that case, multiple reflections are necessary for any light to escape. This ensures that any escaping light may be attenuated by the reflecting surfaces which may be provided with non-reflective surfaces or surface coatings to minimize the escape of light from the discharge opening 614. Thus, the position and orientation of a fin tube heat exchanger may advantageously provide a light blocking function as well as provide minimal resistance to air flow.

In addition, a discharge grill 621 with vanes may be provide to further ensure against the escape of light. Though shown in one discharge, they may be used in both or neither. Note that UVC wavelengths used for germicidal effect are not as harmful as other wavelength ranges such as UVB and UVA so some light may escape. The proximity sensor 623 control may also be used to limit the application of UV during occupancy periods or only allow light to be used for limited times when a room is occupied. This control feature may be employed with any of the disclosed embodiments.

In any of the embodiments disclosed, a supplemental fan may be provided to force air flowing the chilled beam to flow at a higher rate. The fan may be controlled responsively to a local, room, or central thermostat. The fan may be used to accelerate flow to prevent chilling water in the heat exchanger from causing the heat exchanger surfaces from dropping to the dew point.

The chilled beam 601 may also be provided with features to allow the primary air openings forming jets 612 to selectively provide larger volumes of ventilation and return air as described in WO/2011/091380 filed internationally on 24 Jan. 2011, the entirety of which is hereby incorporated by reference herein. In such embodiments, a secondary terminal unit provides heating or cooling effect to a combined primary and return air stream, a return stream only, or a primary stream only. As described in the reference, the secondary terminal unit may provide latent cooling and temperature control of the air stream supplied to the chilled beam 601. The other chilled beams described herein may also be modified as described to work with the secondary terminal unit system arrangement.

Figure 9B:
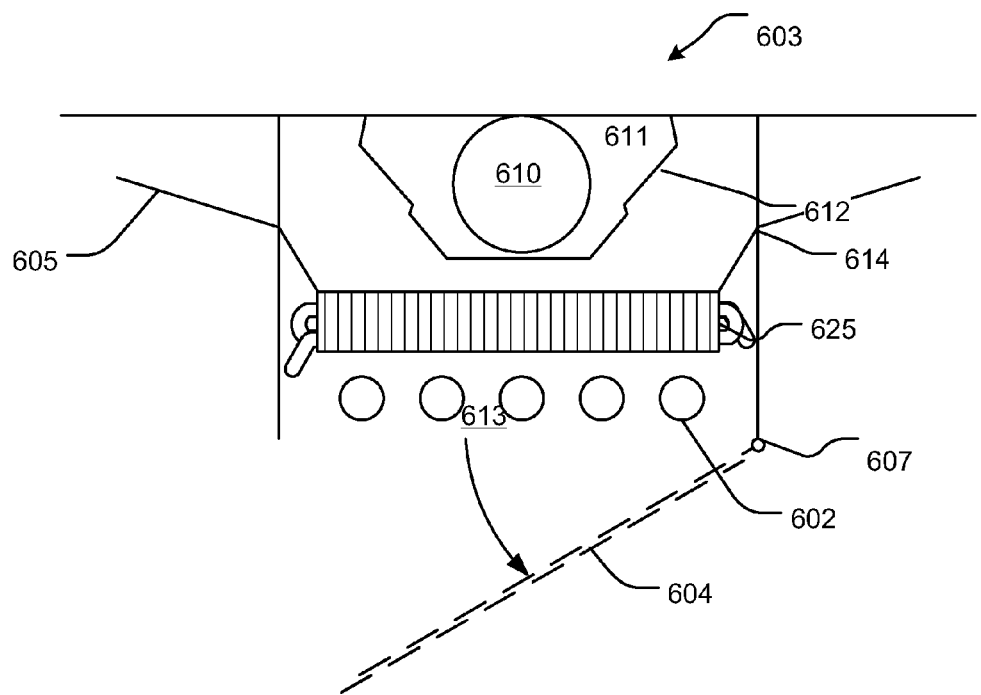

Embodiment 603 of FIG. 9A differs from embodiment 601 in having a heat exchanger 625 whose fins are oriented differently. Also, in FIG. 9B, the intake grill, which pivots on hinge 607, is shown in an open position.

Figure 10A:
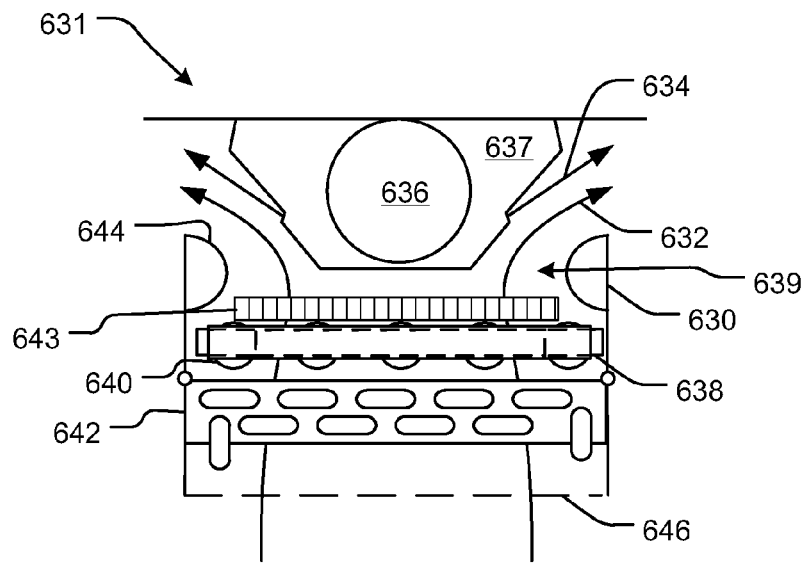
FIGS. 10A and 10B show chilled beams with UV according to further embodiments of the disclosed subject matter.

Referring now to FIG. 10A a chilled beam 631 shown (as are the others) in cross-section, has an inlet or connection collar 636 which supplies primary air to a plenum 637 that runs along the length of the chilled beam terminal unit 631. A heat exchanger 642 (fin tube type for example) cools air rising into intake grill 646 which has offset light-blocking elements, figuratively indicated at 646, but conforming to any of the embodiments described elsewhere in the present disclosure. Lamps 640 generate UV light, for example, UVC or germicidal wavelengths of UV. Light impinges the surfaces of the heat exchanger 642 reducing the risk of the formation of pathogenic cultures on these surfaces. The lamps 640 are supported on a pivot-slide mechanism 639 which can be seen in a stowed position in FIG. 10A and an extended and dropped position in FIG. 10B. An embodiment is configured as a drawer slide with a hinge. The lamps may be electrically connected by an coiled cord or by brushes that maintain contact with hidden conductors in the pivot-slide mechanism 639 or any suitable means. A door 630 has an air guide element 644 which also provides a light blocking function. The air guide may or may not be used. A flow straightener 643 provides another measure of light blocking with minimal resistance to air flow. The flow straightener may have a honeycomb structure, parallel plate structure (for example perpendicular to the fins of the heat exchanger 642) or other similar structure.

Figure 10B:
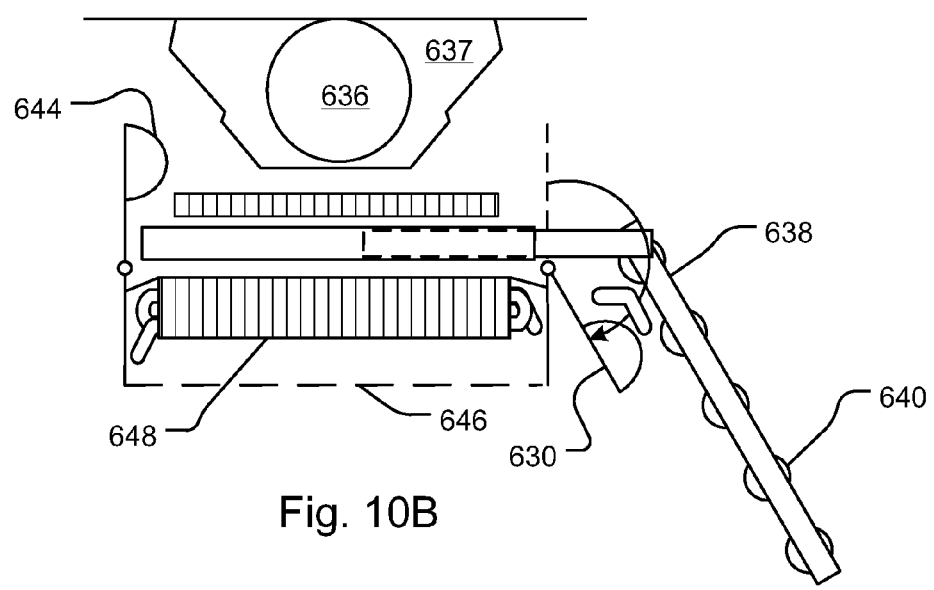

The lamps are preferably supported to position them such that they cause UV light to impinge the heat exchange surfaces of heat exchanger 642. Air flows through the grill 646, through the heat exchanger 642, past the lamps 640, and through the flow straightener 643, finally flowing through the space 639 in which the jet 634 is generated from primary air in the plenum 637. The jet 634 induces a flow in the space 639 causing a negative pressure in the space 639 that draws air through the grill, lamps, and heat exchanger. A flow that includes primary and secondary (entrained) flow 632 is forced upwardly and outwardly as indicated. The lamps 640 also provide germicidal effect on the interior surfaces defining the flow passages of the chilled beam 631. FIG. 10B shows the heat exchanger 648 in a different orientation with the door 630 in the open position for accessing the lamps 640.

Figure 11A:
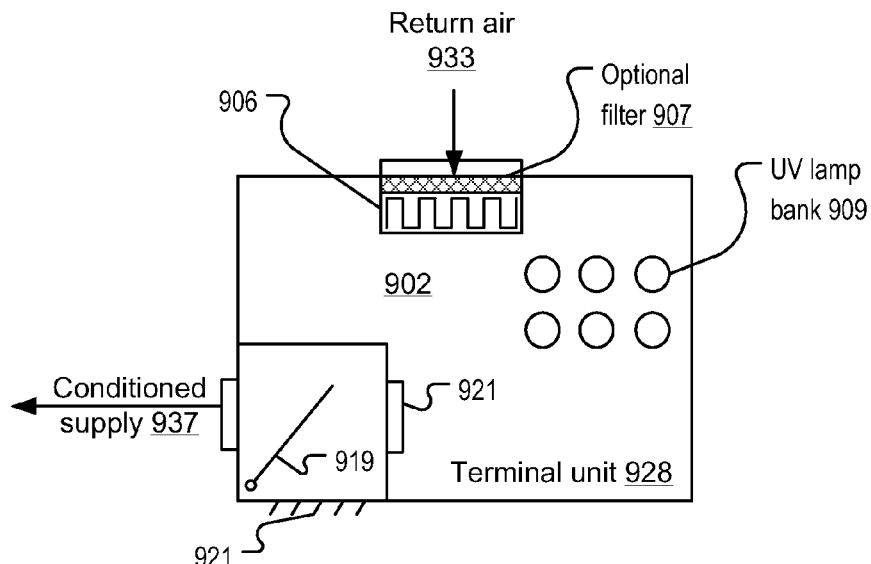
FIGS. 11A and 11B show terminal units for use with chilled beam systems according to embodiments of the disclosed subject matter.

Referring to FIG. 11A, a secondary terminal unit 928 has a flow chamber 902 with a heat exchanger 906 which provides heating or cooling to condition a return air stream 933 flowing from a room in which one or more chilled beams receive air from the conditioned supply 937. A filter 907 may be provided in this and any of the other embodiments. The heat exchanger may be a water cooled liquid/air heat exchanger, an electric air heater, a gas-fired furnace, or any suitable source of heat or cool. Alternatively, the heat exchanger 906 may be a multimode device with one or more heat exchangers or a single switchable heat exchanger that can supply heat and cooling effect or plurality of devices providing, at any given time, a selected one of heating and cooling functions (or both to respective air streams). The conditioned air leaves the terminal unit 928 as a conditioned supply 937. The change in function can be provided, for example, by mode-switched valves connecting a single heat exchanger selectively to one of a chiller and a heater.

In the present embodiment of FIG. 11A or the embodiment of FIG. 11B to be described below, a damper may regulate the proportion of flow to be provided to a direct mixing register 921 (which may be directly connected to the terminal unit or separately by a duct) or the conditioned supply 937 connected to one or more chilled beams. The purpose of providing a different outlet from the chilled beams is that chilled beams are generally designed to provide relatively low primary air volume and once mixed with the induced return flow that passes through the heat exchanger, the mixed air ejected by the beam is of relatively low velocity. If heated air is supplied at low velocity from the ceiling level where the chilled beams are located, there is a tendency for the warm air to remain at a high level and thereby be less effective at providing comfort. By ejecting a flow of air at high velocity and low aspect ratio from a suitable mixing register, the throw of the heated jet can be greater and the comfort effect of the heated stream greater. The damper 419 may be switched in response to mode (heating versus cooling). It may also provide a variable ratio of air between the mixing outlet and the beam outlet. A fan, as discussed with reference to the embodiments of FIG. 11B may also be provided to provide a greater volume rate of flow.

In addition to providing supplementary filtration and temperature conditioning, the terminal unit 928 may also be provided with UV lamps to provide germicidal effect. The UV lamps may be of any type including UVA, UVB, or UVC. The UV lamps may be provided in addition to the filtration and/or temperature conditioning aspects or alternatively to them.

With a higher volume rate including return air directly provided to the terminal unit as well as primary air from the air handling unit, the design beam volume rate may be met whilst still providing additional volume for effective use of the mixing register 921. In an alternative embodiment, a simple damper is used in the mixing register output and at least some air is always permitted to go to the beam output 937. The fan may be a variable rate fan and may be turned off under selected conditions, for example, proportionally in response to higher load, during heating (when the mixing register is used in combination with the beams). Note in some embodiments, the beams may be bypassed in heating mode and a mixing register used alone.

Figure 11B:
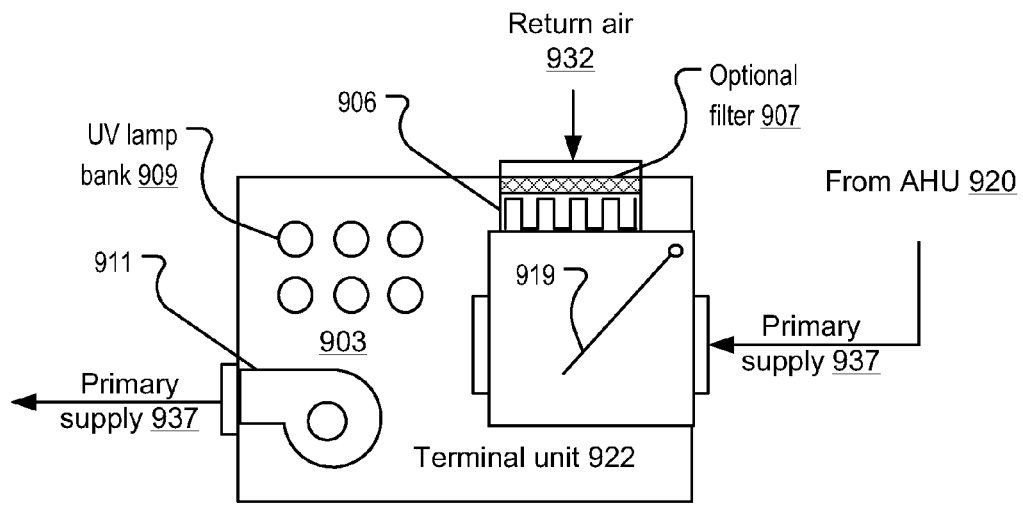

Referring to FIG. 11B the terminal unit 922 has a flow chamber with a heat exchanger 406 which provides heating or cooling to condition the return air stream 932 from the conditioned space. The heat exchanger may be a water cooled liquid/air heat exchanger, an electric air heater, a gas-fired furnace, or any suitable source of heat or cool. Alternatively, the heat exchanger 906 may be a multimode device that can supply heat and cooling effect or plurality of devices providing, at any given time, a selected one of heating and cooling functions. The conditioned return air is mixed with the primary supply air 933 from the air handling unit 920 in a mixing flow chamber 903, which it leaves as the final primary air 930. In any of the embodiments described herein, a fan or other air mover 911 may be provided to provide increased volume flow, capability for balancing flow among local groups of chilled beams, or to overcome additional resistance of the heat exchanger 905, filter 907, or other factors. In addition or alternatively, a damper 917 may be provided in any of the embodiments to allow the variation of the mix of return 932 and supply 933 air in the primary supply 930. As in the 928 embodiment, UV lamps 909 are provided.

In any of the embodiments, a damper 919 may provide for selection of the ratio of primary supply 933 from the air handling unit 920 and the return air 932 from the conditioned space. A fan 911 may be provided as discussed above and shown here. In low profile embodiments of terminal units, for example as discussed later for use with configurations that can fit over a hung ceiling, suitable fan designs such as tangential fans may be employed.

In embodiments of any of the systems described herein, return air passes through a mixing valve configured to exhaust a selectable amount of the return air and replace that amount with fresh air from a fresh air source. The resulting partial stream may be fed to the supply terminal unit.

In embodiments, the terminal unit 928 is configured to permit primary supply air to be tempered by a heat exchanger in addition to the tempering of the return air stream.

In embodiments of the systems described herein, return air passes through a mixing valve configured to exhaust a selectable amount of the return air. The resulting diminished stream is fed to the supply terminal unit. In a further embodiment, the terminal unit has mixes a selectable quantity of fresh air with the conditioned return air.

In any of the embodiments described, various control methods will be recognized as suitable for regulating the rate of heating or cooling required.

In any of the embodiments described, the terminal unit may include a regenerating desiccant to handle at least part of the latent load of the space.

In embodiments of the systems described herein, a terminal unit is retrofitted to an existing chilled beam system which is otherwise configured to provide only cooling. In such a retrofit, the terminal unit adds heating capability to the system.

In any of the embodiments described, a terminal unit is provided as a retrofit to provide an increased heating and/or cooling capacity to an existing chilled beam system.

In a method of providing a chilled beam system, a cooling load is satisfied by designing providing a capacity of a chilled beam air handling unit is based on ventilation requirements which may be ineffective for handling the total cooling load. In the method, the supplemental cooling effect is provided by a terminal unit as in any of the embodiments. In such system, the capacity of the terminal unit is sufficient to satisfy the total cooling load, reduced by the cooling effect provided by the air handling unit. In embodiments, systems are configured with components of the specified relative capacities.

In one or more system embodiments of a chilled beam system, a cooling load is satisfied by designing providing a capacity of a chilled beam air handling unit is based on ventilation requirements which may be ineffective for handling the total cooling load. In the systems, the supplemental cooling effect is provided by a terminal unit as in any of the embodiments.

Much of the foregoing description relates to, and is similar to, the embodiments of the international application incorporated by reference above.

In control embodiments, the heat exchanger and/or desiccant component of the terminal units are shut off when the capacity of the air handling unit is sufficient. In such embodiments, return air may be selectably made to bypass the heat exchanger or desiccant component to reduce pressure losses. In embodiments, the heat exchanger of terminal units 128 or 122 may be replaced with, or combined with, a desiccant enthalpy control device such as a desiccant wheel.

In one or more control embodiments, at times when ventilation load is low such as night-time, the terminal units provide latent and/or sensible load management and the air handling unit is shut down or operated intermittently.

One or more control devices (indicated as "XTL" in the figures) may be provided to control the terminal units, the air handling units or both. In any of the embodiments, the number of air handling units is independent of the number of terminal units.

In any of the embodiments, instead of a desiccant, a condensing heat exchanger may be provided. In any of the terminal unit embodiments, the heat exchanger 906 may be one or more heat exchangers at least one of which may include a condensing coil.

Figure 12A:
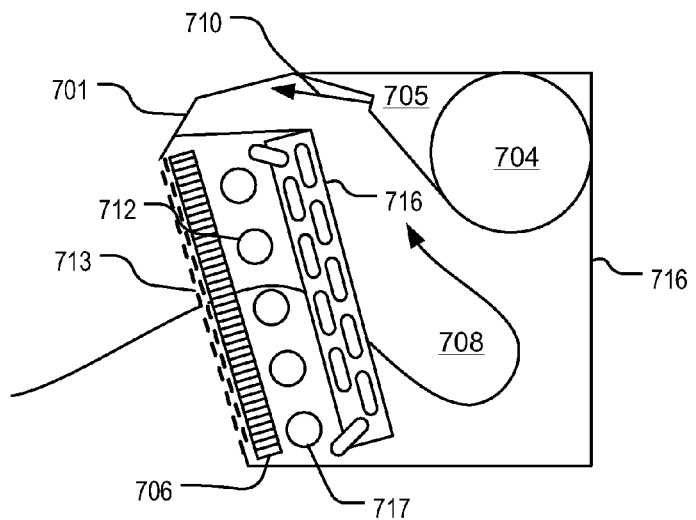
FIGS. 12A and 12B show chilled beams with UV according to further embodiments of the disclosed subject matter.
Figure 12B:
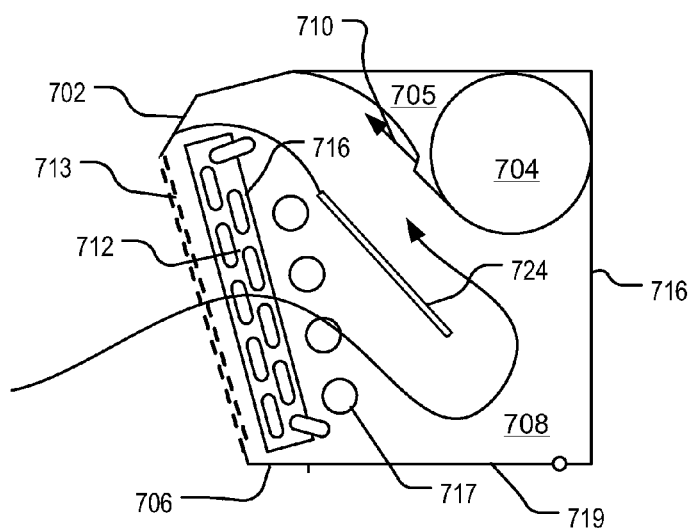

Referring now to FIGS. 12A and 12B, wall mountable chilled beam embodiments 701 and 702 shown (as are the others) in cross-section, have an inlet or connection collar 704 which supplies primary air to a plenum 705 that runs along the length of the chilled beam terminal unit 701. A jet 710 is generated by air pressurized in the plenum 705. The jet induces flow through the apparatus. A heat exchanger 716 (fin tube type for example) cools air drawn into intake grill 713 which has offset light-blocking elements, figuratively indicated at 713, but conforming to any of the embodiments described elsewhere in the present disclosure. Lamps 717 generate UV light, for example, UVC or germicidal wavelengths of UV. Light impinges the surfaces of the heat exchanger 716 reducing the risk of the formation of pathogenic cultures on these surfaces. The lamps 717 may be supported on a slide mechanism as described above or sufficient access may be provided by a hatch 719. An flow straightener 706 may or may not be used in either embodiment. A baffle plate 724 may elongate the flow path of air in the space 708. The baffle plate 724 may be of UV transparent material to permit longer exposure time of the air in the space 708. The flow straightener may have a honeycomb structure, parallel plate structure (for example perpendicular to the fins of the heat exchanger) or other similar structure.

The lamps are preferably supported to position them such that they cause UV light to impinge the heat exchange surfaces of heat exchanger. A flow that includes primary and secondary (entrained) flow is forced upwardly and outwardly as indicated. The lamps also provide germicidal effect on the interior surfaces defining the flow passages of the chilled beam.

Figure 13A:
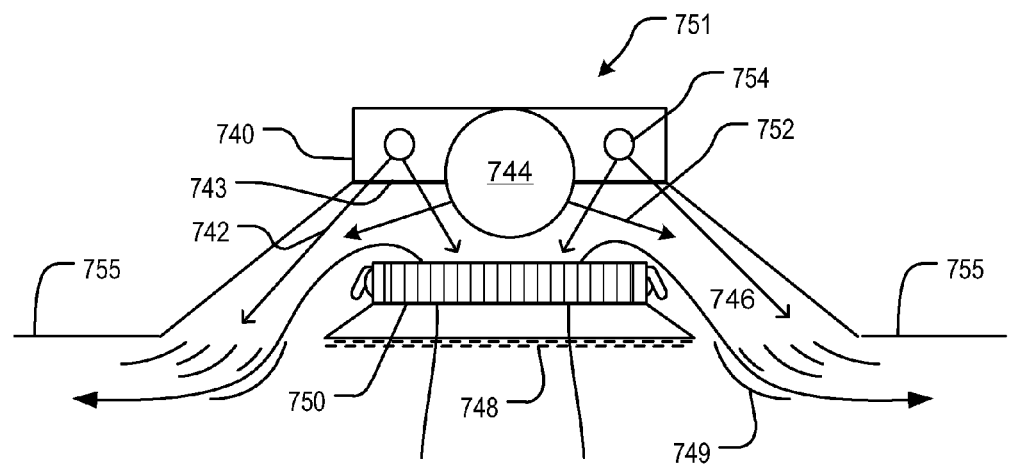
FIGS. 13A and 13B show chilled beams with UV according to further embodiments of the disclosed subject matter.

Referring now to FIG. 13A, a chilled beam 751 suitable for above ceiling mounting has lamps 754 arranged within a box 740 that may form part of a plenum. A collar 744 supplies primary air and may define a duct running along the length of the beam 751 with openings to form primary air jets 752. A UV transparent window 743 permits light 742, 752 to shine on a heat exchanger 750 as well as along a length of an extended straight portion of a flow path 746. Extended flow guides 749 perform the dual function of causing air to flow along the ceiling 755 and blocking any light that would otherwise escape. An inlet grill 748 may be configured as discussed in other embodiments. The lamps 754 may be behind the window 743 or alternatively the window may be omitted. The window 743 may be curved and even if straight as shown may serve an air flow smoothing function.

Figure 13B:
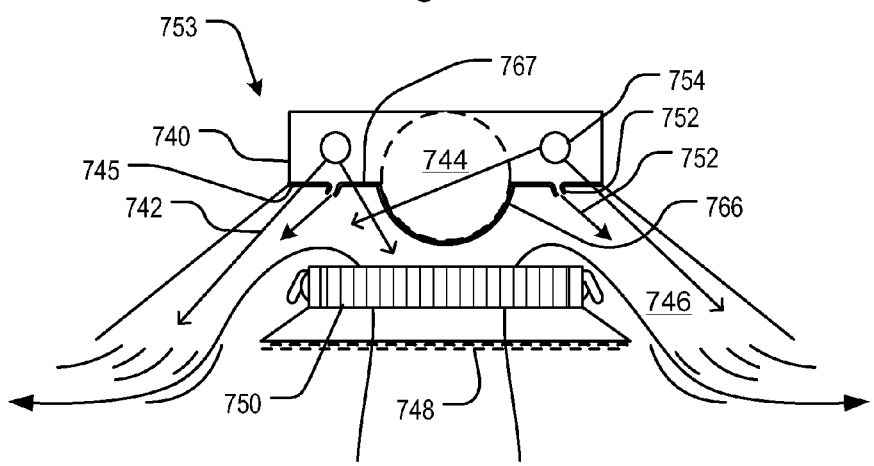

The embodiment 753 of FIG. 13B uses the space inside box 740 as a plenum. Flow nozzles 752 are provided in the window 745 for generating the primary air jet 752. Light from the UV lamps can expose the primary air as well as secondary entrained air circulating through the heat exchanger and can also illuminate the surfaces of the heat exchanger 750.

Figure 14:
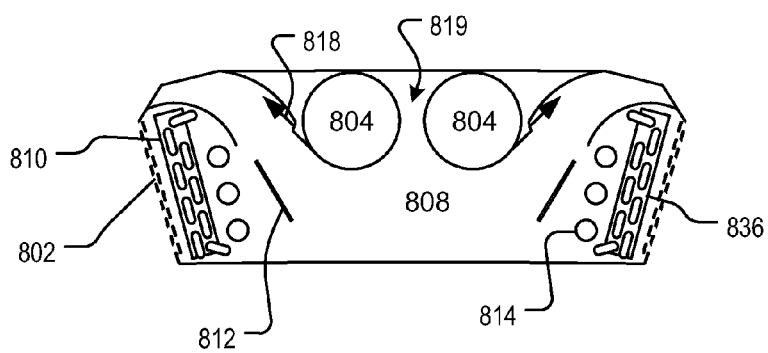
FIG. 14 shows a chilled beam with UV according to further embodiments of the disclosed subject matter.
Figure 15A:
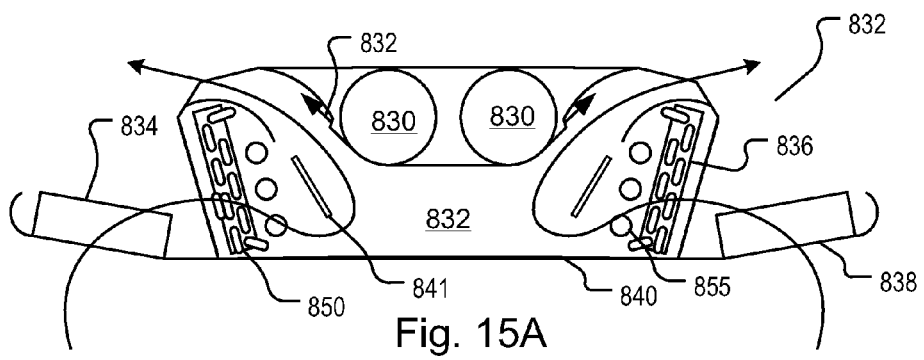
FIGS. 15A through 15C show chilled beams with UV according to further embodiments of the disclosed subject matter.
Figure 15B:
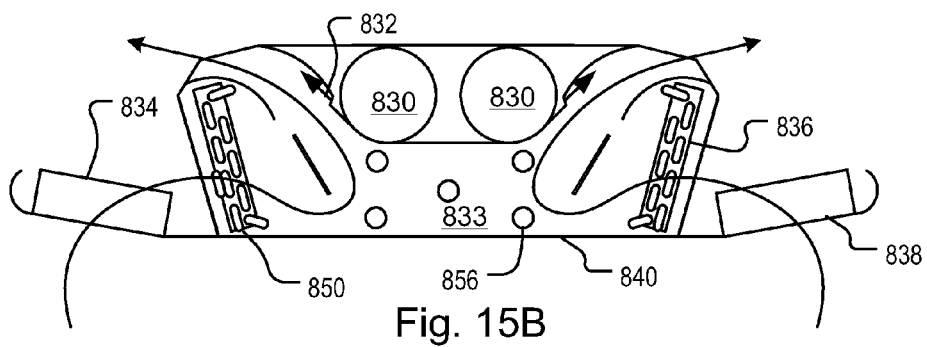
Figure 15C:
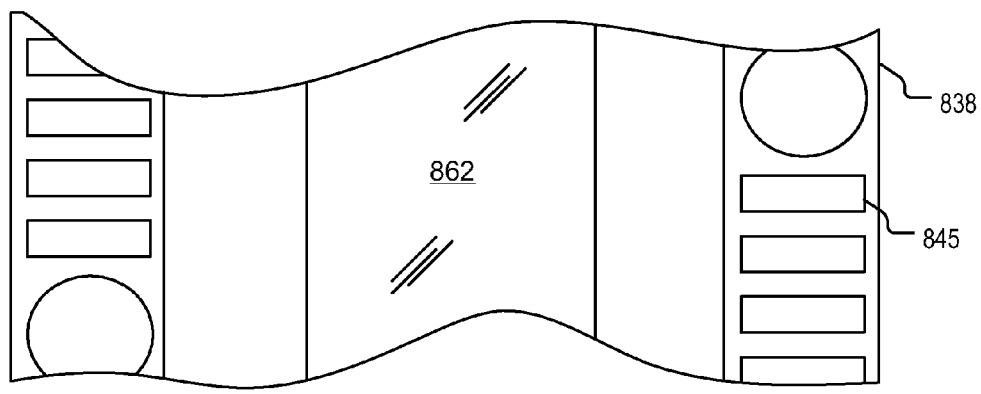

FIG. 14 shows a chilled beam with dual connection collars 840 that supply air to a plenum 819 to generate jets 818. Lamps 814 shine UV into a space 808 through which air circulates. A heat exchanger 836 is illuminated by the lamps as well. Baffle plates help to eliminate short circuit flow of air that would reduce exposure duration. The use of split heat exchangers creates a shallow embodiment with a large central flow space 808. A heat exchange 836 is provided as well. FIG. 15 shows a variation of the FIG. 14 embodiment in which an additional service is provided by a component 834 which may be an occupancy sensor, lights, fire sprinkler or other service. Air flows through gaps in a lower panel 835 as indicated in FIG. 15C. FIGS. 15A and 15B show alternative locations for the UV lamps 855 and 856, respectively. FIG. 15C shows another optional feature in which UV light is converted to visible by a UV to visible converting window 862. Various materials can provide the frequency down-conversion and incorporated in glass or plastic windows as is known in the respective arts. Baffle plates 841, heat exchangers 836, jets 832, connections 830, and flow spaces 832 and 833 provide the same functions as described in the embodiment of FIG. 14. The embodiments of FIGS. 14, and 15A through 15C are arranged to direct air toward a ceiling but may be configured to direct air in other directions with suitable modification.

It is, thus, apparent that there is provided, in accordance with the present disclosure. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention. The drawings illustrate various features that can be used in the respective embodiment or interchanged with other embodiments. For example the heat exchanger configuration of one may be replaced with that of another embodiment. The UV lamp arrangements may be interchanged as well as light directors, flow guides, inlet air diffusers, outlet air diffusers, etc. to form additional embodiments according to the teachings of the present disclosure.

The invention claimed is:

1. A combined cooling, heating and air supply treatment system for a suspended ceiling installation, comprising:
 a housing including an air treatment device and a movable access member which is configured to form an enclosure with the housing when in a first position and to allow access to the air treatment device when in a second position;
 wherein the access member includes a plurality of openings configured to permit passage of ambient air from a space outside of the enclosure into the enclosure, and passage of air treated by the air treatment device from the enclosure to the space outside of it;
 wherein the access member is movable from the first position to the second position by pivotal movement;
 at least one ultraviolet light source attached to an inside portion of the access member, such that the UV light source moves with the access member, said ultraviolet light source generating light in the 240-280 nm range at intensities sufficient to kill microbial contaminants on surfaces and such that direct exposure to people is harmful.

2. A system as claimed in claim 1, wherein in the first position the at least one ultraviolet light source is configured to direct light towards an inside of the enclosure and in the second position the at least one ultraviolet light source is configured to direct light towards the space outside of the enclosure.

3. A system as claimed in claim 2, wherein at least a portion of the plurality of openings include elongated channels to direct ambient air towards the air treatment device and to block direct ultraviolet light from escaping the enclosure.

4. A system as claimed in claim 2, further comprising a motion sensor configured to shut-off the at least one ultraviolet light source responsively to a detection of motion in the space outside of the enclosure.

5. A system as claimed in claim 2, further comprising a remote controlled device configured to turn the at least one ultraviolet light source on and off remotely.

6. A system as claimed in claim 2, wherein the access member includes a first layer with a plurality of first openings and a separate second layer with a plurality of second openings, wherein the layers are positioned such that the plurality of first openings are shifted relative to the plurality of second openings so that ambient air can flow through the first and then the second layer unobstructed and such that direct ultraviolet light does not pass between the first and second openings.

\* \* \* \* \*